US00PP20253P2

(12) United States Plant Patent
Handley

(10) Patent No.: US PP20,253 P2
(45) Date of Patent: Sep. 1, 2009

(54) ***ERYSIMUM* PLANT NAMED 'JENNY BROOK'**

(50) Latin Name: *Erysimum linifolium*
Varietal Denomination: Jenny Brook

(76) Inventor: Roger Handley, Caerolweg, Lon Glanfred, Llandre, Bow Street, Ceredigion (GB), SY24 5BY ( * ) Notice: Subject to any disclaimer, the term of this patent is extended or adjusted under 35 U.S.C. 154(b) by 0 days.

(21) Appl. No.: 12/079,984

(22) Filed: Mar. 31, 2008

(51) Int. Cl.
*A01H 5/00* (2006.01)

(52) U.S. Cl. ..... Plt./263.1

(58) Field of Classification Search ..... Plt./263.1
See application file for complete search history.

(56) References Cited

PUBLICATIONS

Upov Plant Variety Database Mar. 2008 search for PBR 20060957 for cultivar Jenny Brook. p. 1. 2008.*

* cited by examiner

*Primary Examiner*—Annette H Para
(74) *Attorney, Agent, or Firm*—Jondle & Associates, P.C.

(57) ABSTRACT

A new *Erysimum* plant particularly distinguished by flowers which change color through the season starting out as purple-mauve changing to peach and by its upright, long flower stems that are held above green linear foliage is disclosed.

1 Drawing Sheet

Genus and species: *Erysimum linifolium*
Variety denomination: 'Jenny Brook'.

BACKGROUND OF THE NEW PLANT

The present invention comprises a new and distinct cultivar of *Erysimum,* botanically known as *Erysimum linifolium* and hereinafter referred to by the cultivar name 'Jenny Brook'. The new cultivar was discovered in a cultivated garden in Cerdigion, Wales in 2001. Both the male and female parents are unknown individual plants of *Erysimum.* 'Jenny Brook' was first propagated in 2001 in Cerdigion, Wales.

The new cultivar was discovered in Cerdigion, Wales in 2001 and has been asexually reproduced repeatedly by vegetative cuttings over a 7-year period in Cerdigion, Wales and Lancaster, Pa. The present invention has been found to retain its distinctive characteristics through successive asexual propagations.

Plant Breeder's Rights for this cultivar were applied for in the European Union on Apr. 19, 2006. 'Jenny Brook' has not been made publicly available more than one year prior to filing of this application.

SUMMARY OF THE INVENTION

The following are the most outstanding and distinguishing characteristics of this new cultivar when grown under normal horticultural practices in Cerdigion, Wales and Lancaster, Pa.

1. Flowers change color through the season starting out as purple-mauve changing to peach; and
2. Upright, long flower stems that are held above green linear foliage.

DESCRIPTION OF THE PHOTOGRAPH

This new *Erysimum* plant is illustrated by the accompanying photograph which shows a close-up of the inflorescence; the colors shown are as true as can be reasonably obtained by conventional photographic procedures.

DESCRIPTION OF THE NEW CULTIVAR

The following detailed descriptions set forth the distinctive characteristics of 'Jenny Brook'. The data which define these characteristics were collected from asexual reproductions carried out in Lancaster, Pa. The plant history was taken on one-year-old plants grown outdoors. Color readings were taken outdoors under natural light. Color references primarily to the R.H.S. Colour Chart of The Royal Horticultural Society of London (R.H.S.) (2001 edition).

DESCRIPTION OF THE NEW PLANT

Classification:
- *Family.*—Brassicaceae.
- *Botanical.*—*Erysimum linifolium.*
- *Common name.*—Perennial wallflower.

Parentage:
- *Female parent.*—Unknown.
- *Male parent.*—Unknown.

Plant:
- *Type.*—Perennial.
- *Habit.*—Woody base, branching, numerous linear shaped leaves.
- *Height (from top of soil).*—60.0 cm.
- *Width (horizontal plant diameter).*—60.0 cm.
- *Propagation.*—Tip cuttings, tissue culture.
- *Time to produce a finished flowering plant.*—8 weeks.
- *Time to initiate and develop roots.*—10 days.
- *Root description.*—White, fibrous.

Stems:
- *Average number.*—8.
- *Length of stems/branches (from the base of the stem to the tip).*—20.0 cm.
- *Internode length.*—0.5 cm.
- *Diameter of branches (from midpoint).*—0.3 cm.
- *Stem color.*—RHS 137A (Green).

*Anthocyanin.*—RHS 59A to RHS 59B (Red-Purple).
*Texture.*—Rough.

Leaves:
*Arrangement.*—Alternate.
*Size.*—Length: 5.0 cm to 11.0 cm. Width: 0.5 cm.
*Shape.*—Linear.
*Apex.*—Acute.
*Base.*—Cuneate.
*Margin.*—Undulate.
*Texture.*—Upper surface: Rough. Lower surface: Smooth.
*Immature leaf.*—Color: Upper surface: RHS 137B (Green). Lower surface: RHS 137C (Green).
*Mature leaf.*—Color: Upper surface: RHS 137A (Green). Lower surface: RHS 137D (Green).
*Venation pattern.*—Pinnate, very faint.
*Venation color.*—Upper surface: RHS 137A (Green). Lower surface: RHS 137D (Green).
*Petioles.*—Absent.

Flower bud:
*Shape.*—Elliptic.
*Size.*—Length: 0.5 cm. Diameter: 0.3 cm.
*Color at tight bud.*—RHS 59A (Red-Purple).
*Texture.*—Smooth.

Inflorescence:
*Blooming habit* (*flowering season*).—May to July and August.
*Inflorescence type.*—Raceme.
*Average number of flowering stems.*—20.
*Average number of flowers and buds per stem.*—30.
*Lastingness of individual blooms on the plant.*—10 days.
*Fragrance.*—Slight.
*Inflorescence length.*—30.0 cm to 40.0 cm.
*Inflorescence diameter.*—5.0 cm.

Flowers:
*Type.*—Single flower, four petals, borne in dense elongating corymb like racemes.
*Shape.*—Cruciform.
*Size.*—Length or depth: 2.0 cm. Width or diameter: 3.0 cm.
*Petals.*—Number per flower: 4. Length: 1.0 cm. Width: 1.0 cm. Shape: Obocordate. Apex: Retuse. Base: Attenuate. Margin: Entire. Texture: Upper surface: Smooth. Lower surface: Smooth. Color: Upper surface: RHS 35C (Orange-Red). Lower surface: RHS 35D (Orange-Red).
*Calyx arrangement.* —Tubular, deeply cut to form 4 segments.
*Sepals.*—Quantity per flower: 4. Length: 1.0 cm. Width: 0.3 cm. Shape: Tubular. Apex: Acute. Base: Cuneate. Margin: Entire. Texture: Upper surface: Slightly rough. Lower surface: Smooth. Color: Upper surface: RHS 59A (Red-Purple). Lower surface: RHS 59D (Red-Purple).

Peduncles:
*Length.*—30.0 cm to 40.0 cm.
*Diameter.*—0.5 cm.
*Aspect.*—Erect.
*Texture.*—Rough.
*Color.*—RHS 137A (Green).

Pedicels:
*Length.*—1.0 cm.
*Diameter.*—0.2 cm.
*Texture.*—Slightly rough.
*Color.*—RHS 137A (Green).

Reproductive organs:
*Stamens.*—Quantity per flower: 5. Filament length: 0.8 cm. Filament diameter: 0.1 cm. Anthers: Shape: Ligulate Length: 0.3 cm. Diameter: 0.1 cm. Color: RHS 152A (Yellow-Green). Pollen amount: Very sparse. Pollen color: RHS 153A (Yellow-Green).
*Pistils.*—Number per flower: 1. Length: 1.0 cm. Diameter: 0.1 cm. Stigma: Length: 0.01 cm. Diameter: 0.1 cm. Shape: Rounded. Color: RHS 150C (Yellow-Green). Style: Length: 0.9 cm. Diameter: 0.1 cm. Shape: Tubular. Color: RHS 150C (Yellow-Green).

Fruit and seed set: Has not been observed.
Disease and insect resistance: Typical of *Erysimum.*

COMPARISON WITH COMMERCIAL CULTIVARS

'Jenny Brook' differs from the commercial cultivar 'Bowles Mauve' (unpatented) in that 'Jenny Brook' has flowers that change color through the flowering season from purple-mauve to peach, while 'Bowles Mauve' has flowers that are lilac and pink.

I claim:

1. A new and distinct cultivar of *Erysimum* plant as shown and described herein.

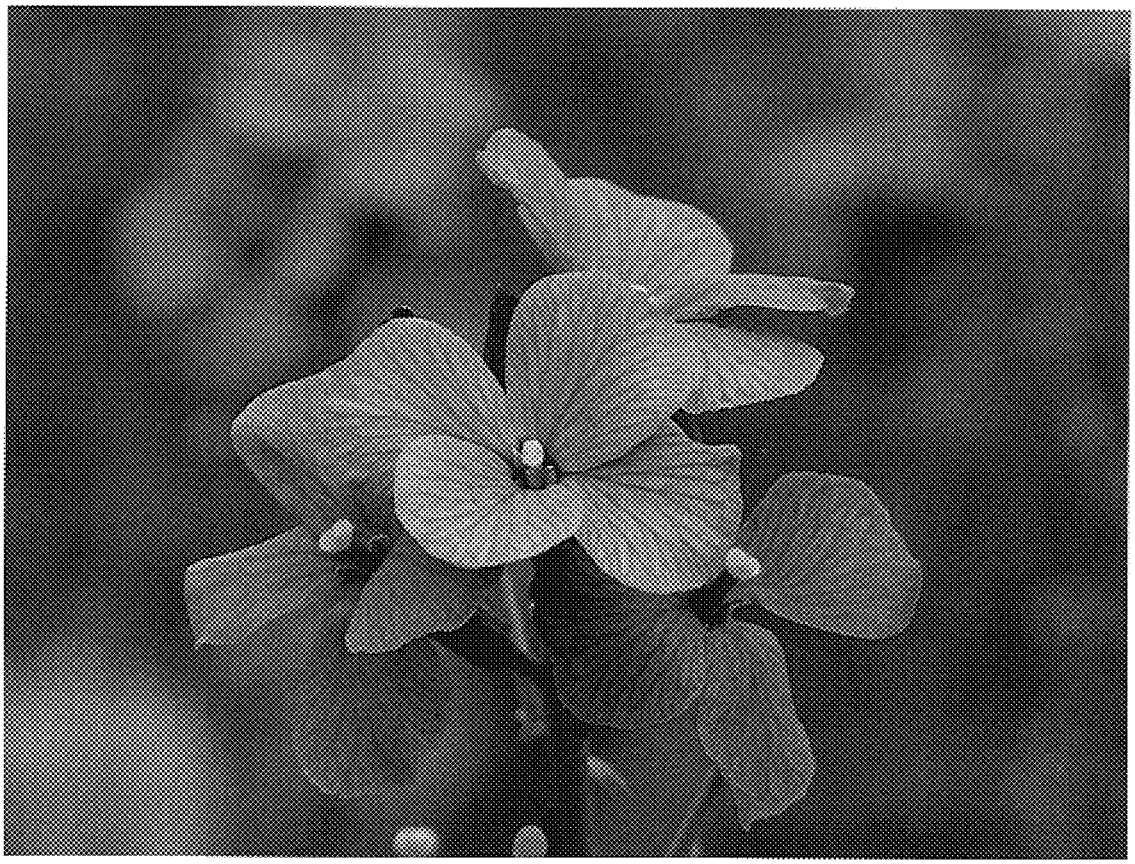

* * * * *